Jan. 11, 1949. C. C. ALLER Plant Pat. 819
APPLE TREE
Filed Jan. 22, 1947
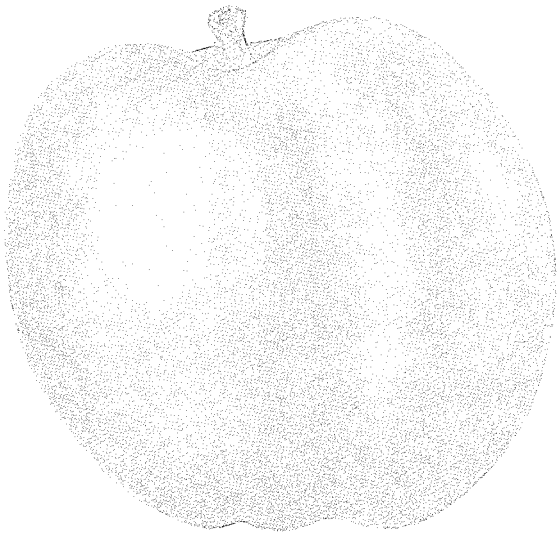
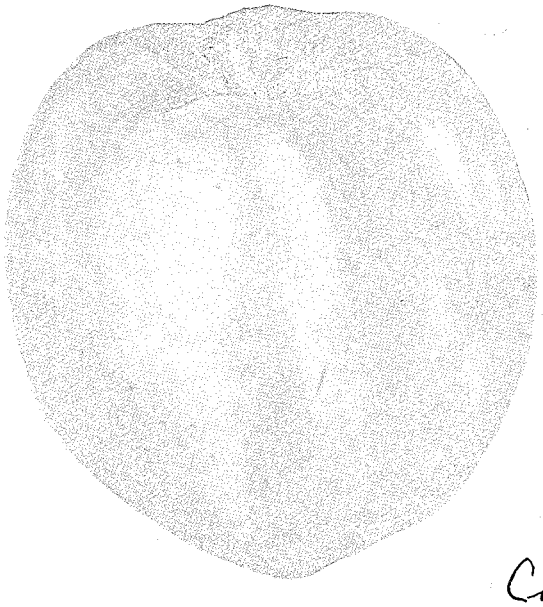
INVENTOR
Curtis C. Aller
By Oriella M. Kile
PLANT PATENT AGENT Patented Jan. 11, 1949

Plant Pat. 819

UNITED STATES PATENT OFFICE

819

APPLE TREE

Curtis C. Aller, Yakima County, Wash.

Application January 22, 1947, Serial No. 723,542

1 Claim. (Cl. 47—62)

The present discovery relates to a new variety of apple of the Newtown type. It originated as a sport of a Yellow Newtown in my nurseries and apparently is identical with its parent in foliage, tree type, and growth. Its fruit also appears to be identical in color, flavor, texture and juiciness of the flesh. I have budded this new variety onto a number of Rome variety trees and the fruit produced is identical with the original sport.

Outstanding among the novel features of this new variety are the long stem and fruit spur which permit the apples to be picked without pulling off either the stem or the fruit spur and without bruising the fruit. This enables the pickers to harvest a much larger volume of marketable apples and also to preserve the spurs for the next season's crop. Also outstanding in the variety are its keeping qualities. All storage tests have shown that the fruit is free from bitter pit and scald and that it keeps much longer than fruit of the parent variety. The combination of these features with the good eating quality of the fruit assures a good volume of highly marketable apples each year.

These features, together with the somewhat elongated and blocky shape of the fruit, have been observed at Yakima, Washington, over a period of five years, and have proved to be constant not only in the original sport but also in succeeding generations of budded trees.

The accompanying illustration shows two views of a specimen of the fruit in such position as to reveal the length of stem and depth of cavity as well as the color of the skin.

Any standard description of the Yellow Newtown tree, such as "Apples of New York" will describe the tree of my new variety, but a detailed description of the fruit of my variety is given below.

*The fruit*

Form: Somewhat long and blocky. Usually unsymmetrical.

Cavity or calyx cup: Deep and pronounced; frequently with russet overlay which extends outside the cavity.

Skin: Thin; tough; smooth; waxy with slight bloom.

Flesh: Juicy; crisp; firm; sprightly; cream tinged with green around core.

Color: Brighter green than the fruit of the parent variety. Color in usual picking stage is between clear Dull Green-Yellow and Dull Green Yellow (Plate XVII, Ridgway's Color Standards), with a more or less winged design in russet extending outward from the cavity. Sometimes there is a slight cinnamon blush on one side. When the fruit is fully ripened, more yellow is present in the color.

Size: Medium. Axial and transverse diameters are approximately equal, being around 3 inches.

Core: Small, surrounded by a definite green ring.

Fruit spurs: Long; separate easily from fruit in picking.

Stems: Sturdy; long, extending above cavity.

*Comparison*

My new variety is identical with the Yellow Newtown in foliage, growth, tree type, and fruit flesh, but differs from that variety principally as follows:

1. My new variety is a somewhat elongated blocky type apple while the Yellow Newtown is a flat type.

2. Calyx cup or cavity of my new variety is deep and pronounced, in keeping with the long type apple, whereas the cavity of Yellow Newtown is flat and very small.

3. The color of the skin of my variety is a much brighter green.

4. The stem of my variety is distinctly long like that of a Delicious, while that of Yellow Newtown is short and stocky.

5. My new variety is free from scald or bitter pit, whereas Yellow Newtown is quite susceptible to both.

6. Fruit spurs of my variety are longer than those of Yellow Newtown and seldom cling to the fruit when picked, whereas they frequently go along with the fruit of Yellow Newtown when picked.

7. My variety bears annually while in most instances the Yellow Newtown bears biennially.

Having thus disclosed my discovery, I claim:

The new and distinct variety of apple tree, substantially as herein shown and described, identical with the Yellow Newtown in foliage, growth, tree type and fruit flesh, but characterized as to novelty by its long fruit spurs which easily separate from the fruit in picking; its freedom from susceptibilty to scald or bitter pit; its habit of bearing annually; and its somewhat elongated blocky fruit having bright green color, deep cavity, and long stems.

CURTIS C. ALLER.

No references cited.